(12) United States Patent
Sluggett et al.

(10) Patent No.: US 12,076,532 B2
(45) Date of Patent: Sep. 3, 2024

(54) ASSEMBLIES, SYSTEMS AND METHODS FOR PROGRAMMING MEDICAL DEVICES

(71) Applicant: Infusion Innovations Pty Ltd., Findon (AU)

(72) Inventors: Andrew Sluggett, Rostrevor (AU); Danny Djurasevich, Utley Park (AU); Paul Crockett, Fairview Park (AU)

(73) Assignee: Infusion Innovations Pty Ltd., Findon (AU)

( * ) Notice: Subject to any disclaimer, the term of this patent is extended or adjusted under 35 U.S.C. 154(b) by 0 days.

(21) Appl. No.: 18/114,961

(22) Filed: Feb. 27, 2023

(65) Prior Publication Data

US 2023/0355873 A1 Nov. 9, 2023

Related U.S. Application Data

(63) Continuation of application No. 16/630,464, filed as application No. PCT/AU2018/050721 on Jul. 12, 2018, now abandoned.

(30) Foreign Application Priority Data

Jul. 12, 2017 (AU) ................................ 2017902740

(51) Int. Cl.
*A61M 5/172* (2006.01)
*G16H 20/17* (2018.01)

(52) U.S. Cl.
CPC ............ *A61M 5/172* (2013.01); *G16H 20/17* (2018.01); *A61M 2205/3584* (2013.01); *A61M 2205/52* (2013.01); *A61M 2207/00* (2013.01)

(58) Field of Classification Search
None
See application file for complete search history.

(56) References Cited

U.S. PATENT DOCUMENTS

2001/0041869 A1* 11/2001 Causey, III ......... A61M 5/1456
604/152
2004/0064041 A1* 4/2004 Lazzaro ............ A61M 5/14546
604/152

(Continued)

FOREIGN PATENT DOCUMENTS

EP 3088021 A1 11/2016
WO 2001070307 A1 9/2001

(Continued)

*Primary Examiner* — Manuel A Mendez
(74) *Attorney, Agent, or Firm* — FRESH IP PLC; Clifford D. Hyra; Aubrey Y. Chen

(57) ABSTRACT

The present invention relates to medical device programming assemblies, systems and methods for programming a medical treatment parameter on a medical device, via a programming key. The programming key may be adapted to mate with the medical device which comprises a programmable, non-transitory, computer readable storage device. The storage device comprises a data connector which is configured to mate with a corresponding data connector on the medical device. The storage device may be affixed to a fastener coupling configured to mate with a corresponding coupling on the medical device when the data connector is brought into proximity with the corresponding data connector on the medical device. The programming key is configured to occupy a space formed within the medical device when the data connector and fastener coupling are mated with the corresponding data connector and fastener coupling of the medical device.

17 Claims, 5 Drawing Sheets

(56) References Cited

U.S. PATENT DOCUMENTS

| | | |
|---|---|---|
| 2008/0009787 A1 | 1/2008 | Jacobsen et al. |
| 2011/0130746 A1* | 6/2011 | Budiman ............... G16H 50/20 |
| | | 604/890.1 |
| 2011/0137281 A1* | 6/2011 | Tang ....................... A61M 5/30 |
| | | 604/500 |
| 2012/0179130 A1 | 7/2012 | Barnes |
| 2015/0148615 A1 | 5/2015 | Brennan et al. |

FOREIGN PATENT DOCUMENTS

| | | | |
|---|---|---|---|
| WO | 2011113435 A1 | 9/2011 | |
| WO | 2015126721 A1 | 8/2015 | |
| WO | 2016041869 A1 | 3/2016 | |
| WO | WO-2017051271 A1 * | 3/2017 | ........... A61B 5/0022 |

\* cited by examiner though in some cases such as serving multiple patients in a busy clinic, nursing staff may not notice or be able to attend to such alarms quickly enough to prevent harm. Data collected by smart pumps can also be uploaded to servers for statistical analysis where it can be used to identify weaknesses in practice and areas for improvement in training.

ASSEMBLIES, SYSTEMS AND METHODS FOR PROGRAMMING MEDICAL DEVICES

This application claims priority from Australian Patent Application No. 2017902740 filed 12 Jul. 2017; and is related to PCT Application No AU/2017/0500195 filed 12 Jan. 2017. The content of both documents is hereby incorporated in their entirety by reference.

TECHNICAL FIELD

The present invention relates generally to medical device programming assemblies, systems and methods for programming a medical treatment parameter on a medical device, via a programming key.

BACKGROUND

Assistive and diagnostic medical devices such as prostheses, electrocardiographs, blood pressure monitors, MRI scanners, catheters, pacemakers, and dialysis machines have been used for decades to diagnose and alleviate various medical conditions. These medical conditions may include acute medical conditions such as infections, myocardial infarction and the like, as well as chronic medical conditions such as diabetes, arthritis, cancer and others.

In recent decades, more sophisticated electronics have been incorporated in many devices. For example, hospital beds are available which incorporate a variety of functions including the ability to weigh the patient, the ability to monitor the position of the patient or the bed frame itself, or the ability to perform various therapeutic functions including vibration therapy or pressure therapy. For medical devices including electrocardiographs, spirometers, artificial pacemakers, infusion pumps, transfusions devices and the like, digital interfaces have been incorporated into the design of products to assist in their programming. Similar trends have also arisen for modern infusion pumps. These, however, have failed to completely displace mechanical infusion pumps, in particular elastomeric infusion pumps.

Infusion pumps are medical devices that deliver infusion therapies (including fluids, nutrients and medications) into a patient's body in a controlled manner via the parenteral route of administration. These infusion systems are the primary means for administering ambulatory parenteral therapies, particularly in the home setting. A wide variety of infusion pumps are now available to accommodate the growing number of medical indications requiring in-line fluid administration.

Modern pharmaceutical treatments now indicate uses involving a wide range of compounds from very small molecules to very large compounds and biologics, a variety of dosage regimens from very small to very large doses, from very small to very large volumes, continuous doses over very short periods to much longer periods, or very specific delivery regimens of pharmaceutical combinations.

The rapid rise in conditions requiring treatment with parenteral medications, such as infections, iron deficiencies, immune and inflammatory disorders, cancer and palliative illnesses, has resulted in an increased demand for acute care hospitals to provide infusion services. In turn, this has created a fiscal pressure on hospitals, competition for infusion chairs in hospital outpatient clinics, and indirect patient costs associated with time spent attending hospital and waiting in waiting rooms for infusions. As a result, both patients and allied health professionals are adopting modern medical devices, some of them quite complex, to manage their own health or to provide care in home.

Many in-line pharmaceutical treatments are administered over extended periods requiring administration using portable infusion pumps rather than stationary infusion pumps which are often used in hospital settings. In addition to providing the patient mobility away from the bedside, ambulatory infusion pumps also provide the added advantage of patient treatment in specialised clinics, in home or as hospital outpatients.

Ambulatory infusion pumps are generally smaller than stationary infusion pumps and are either mechanically driven pumps or battery fuelled, electrically driven pumps, with mechanical elastomeric pump still the most common choice for ambulatory infusions. However, a number of variables can alter the flow rate administered via elastomeric pumps. Hypobaric conditions can decrease infusion rate (Mizuuchi, M and Namiki, A, 2003), variations in temperature, viscosity, duration of storage, back pressure, atmospheric pressure and partial filling can affect flow rate (Skryabina, E A and Dunn, T S, 2006; Irish Medicines Board, 2008) and overfilling or underfilling the balloon can also vary the infusion rate. Indeed, the partial filling of elastomerics results in reported delivery rate inaccuracies of up to 34% (Skryabina, E A and Dunn, T S, 2006).

Despite these difficulties, elastomeric infusion pumps are still widely used as they are simple to operate and therefore offer reliability of functioning over accuracy or consistency of dosage. They are simple, inexpensive, single use, disposable devices.

Most infusion pumps offer much greater accuracy than elastomeric infusion pumps. They have been estimated to have a general accuracy of +/−3-6%. They generally comprise a pump mechanism, such as a peristaltic pump. Peristaltic mechanisms may be linear or rotary and comprise a set of moving fingers, rollers or cams which section off a volume of fluid and propel it through the patient's administration set. The rate of delivery of fluid to the patient is controlled by the size of the fingers, rollers or cams, by restrictors or other flow rate adjustors added to the system, and the speed at which the fingers, rollers or cams move.

However, safety concerns in the use of these devices have arisen from 'free flow' incidents whereby incorrectly fitted administration sets combined with rollers, fingers or cams inadvertently left in the open position have resulted in the gravity feeding of fluid to the patient at much greater rates than those intended. Mechanisms such as fork clamps and valves have been incorporated into administration sets to avoid these incidents, however these mechanisms fall well short of providing fail-safes. Other pump mechanisms, such as those involving a piston, cylinder or the valve assemblies have been implicated in similar performance failures.

Given that parenteral therapies are more rapid and lead to higher systemic drug concentrations compared with other delivery methods, adverse drug events tend to be more rapid and severe when associated with infusions. Therefore, safety remains a major concern for infusion pumps. While accuracy remains a significant issue for elastomeric pumps, failure rates of electric pumps also remain high.

'Smart pumps' have emerged to improve the safety of general infusion pumps. They include dose error reduction systems executed by programs that detect excessive doses of a medicine or programming errors. The more sophisticated systems provide customised drug libraries alerting users to predetermined minimum and maximum dose limits for each drug. They also include alarms that automatically trigger warning signals or safety protocols when incidents occur, such as the detection of air or an occlusion in the administration set, or an indication when the fluid vessel is empty. However, immediate access to skilled personnel is required to rectify errors displayed on 'smart pumps' and to set the pump to resume the correct administration protocol. A more complete review of the complex challenges associated with human responses to 'hard' and 'soft' alerts is provided elsewhere (Reston, J, 2013).

Improvements in pumping mechanisms, including the use of stepper motors, DC motors and motorload sensors, power supplies, switch-mode voltage regulators, and low dropout linear regulators, which in turn improve performance and enable the use of sophisticated microprocessors, have been made to improve the safety of these devices. Regulators now recommend using pumps with safeguards, especially within ambulatory care settings, particularly those comprising safety features such as dose alerts, dosing and flow rate limits, operator feedback (identifying programming errors) and the like.

However, as the sophistication of infusion pumps grows, so too does the need for specialised personnel to maintain and operate the devices. Complex interfaces for programming medical treatment parameters can confuse operators, particularly those involving unclear instructions, warnings messages or unexpected alarms. Sophisticated instrumentation involving complex processing also increases the likelihood of software failures, which has been recognised by the USFDA as the source of a cohort of infusion pump malfunctions (USFDA, 2010).

There is increasing evidence to show that smart pumps are not improving error rates. For example, it has been found that carers violated infusion practice 25% of the time by bypassing drug libraries during the intervention periods, and medications were administered without physician documentation 7.7% of the time.

Smart pumps are not being programmed to provide hard alerts, therefore, it has been easy for carers to override alerts or bypass a drug library. In many cases, poor carer compliance arising from the complexity of smart pump operation overrides the many advantages offered by smart pump decision support.

Modern medical devices, including infusion pumps, are complicated and time-consuming for patients or allied health professional to program and use. Medical facilities such as hospitals often struggle to provide appropriate staffing levels and training for the variety of devices that may be in use at any given time, which presents an additional burden on resources. Human error in pump programming or software errors can have adverse or even deadly consequences for the patient (ISMP, 2007).

The need for improved interfaces for programming medical devices is critical to maintain efficiency of patient care and to reduce potential clinical errors. The safe and effective use of high-risk medications in the home care setting requires an ambulatory infusion pump to deliver the treatment accurately and safely with patient and health care provider acceptance.

It is important to recognize that users, both patients and allied health professionals alike, may be affected by their own emotional states. They may be overwhelmed by the complexity of the medical device or they may be concerned about the possibility of harm (to the equipment, to the patient, or to themselves) if they make an error. Device instructions may be confusing, and users may have insufficient preparation and insufficient personal or institutional support for the use of the device. Regardless of their capabilities, individuals using medical devices must be able to use the devices safely and effectively without compromising the health of the person receiving care (Kaye and Crowley, 2000).

Following a medical treatment, such as a pharmaceutical infusion, most modern medical devices are unable to monitor and record the actual treatment received by the patient, should an error have occurred with the medical device. This is of particular importance for patients receiving in home care where failures or errors of medical devices may be more likely to occur without detection.

Connected devices are in higher demand due to the increasing needs of patients, allied health professionals and clinicians to be aware of the medication or treatment administered to the patient in an ambulatory setting. For smart medical devices which sense these and other parameters, detected data streams may offer the ability to better monitor patient outcomes and if required, adapt treatment regimes.

SUMMARY

In one broad form, embodiments of the invention relate to medical device programming assemblies for programming a medical treatment parameter on a medical device configured to receive a programming key comprising; a programming key adapted to mate with the medical device further comprising, a programmable, non-transitory, computer readable storage device comprising a data connector wherein the data connector is configured to mate with a corresponding data connector on the medical device, the storage device affixed to a fastener coupling configured to mate with a corresponding coupling on the medical device when the data connector is brought into proximity with the corresponding data connector on the medical device, wherein the programming key is configured to occupy a space formed within the medical device when the data connector and fastener coupling are mated with the corresponding data connector and fastener coupling on the medical device.

Medical device programming assemblies according to embodiments may comprise a data hub device adapted to receive data transmitted from the medical device, and adapted to store the data, process the data or communicate the data to the same or another electronic device.

Medical device programming assemblies may further comprise; a medical device comprising, a central processing unit, and a storage device reader wherein the medical device is configured to define a space for receiving the programming key when the data connector and fastener coupling on the medical device are mated with the corresponding data connector and fastener coupling of the programming key.

Further, the data hub device may comprise a server or a router.

Certain embodiments may relate to methods of manufacturing medical device programming assemblies. Such methods may comprise the steps of; obtaining a programmable, non-transitory, computer readable storage device comprising a data connector wherein the data connector is configured to mate with a corresponding data connector on the medical device, programming the programmable, non-transitory, computer readable storage device to encode one or more medical treatment parameters for operating the medical device, and affixing the storage device to a fastener coupling configured to mate with a corresponding coupling on the medical device when the data connector is brought into proximity with the corresponding data connector on the medical device.

Certain methods may also comprise the step of programming the programmable, non-transitory, computer readable storage device and the subsequent step of rendering the medical treatment parameter substantially non-editable.

In a further broad form, embodiments of the invention may relate to systems for programming a medical treatment parameter on a medical device configured to receive a programming key comprising; a programming key adapted to mate with the medical device further comprising, a programmable, non-transitory, computer readable storage device comprising a data connector wherein the data connector is configured to mate with a corresponding data connector on the medical device, the storage device affixed to a fastener coupling configured to mate with a corresponding coupling on the medical device when the data connector is brought into proximity with the corresponding data connector on the medical device, wherein the programming key is configured to occupy a space formed within the medical device when the data connector and fastener coupling are mated with the corresponding data connector and fastener coupling on the medical device.

Certain systems may comprise a data hub device adapted to receive data transmitted from the medical device, and store the data, process the data or communicate the data to the same or another electronic device. Others may comprise; a medical device comprising, a central processing unit, and a storage device reader wherein the medical device is configured to define a space for receiving the programming key when the data connector and fastener coupling on the medical device are mated with the corresponding data connector and fastener coupling of the programming key.

In one form, systems may be characterised wherein; the programmable, non-transitory, computer readable storage device is affixed to a fastener coupling, and the medical device comprises, an opening adapted to receive the programmable, non-transitory, computer readable storage device, and a fastener coupling adapted to receive and secure to the fastener coupling.

In a further broad form, embodiments of the invention may relate to methods for the transfer of data from a programmable, non-transitory, computer readable storage device to a data hub device comprising the steps of; obtaining a programming key further comprising, a programmable, non-transitory, computer readable storage device encoding a medical treatment parameter for operating a medical device, further comprising a data connector wherein the data connector is configured to mate with a corresponding data connector on the medical device, obtaining the medical device further comprising, a central processing unit, and a storage device reader comprising a data connector wherein the data connector is configured to mate with a corresponding data connector on the storage device, mating the storage device data connector with the medical device data connector, communicating the medical treatment parameter to the medical device, and communicating the medical treatment parameter from the medical device to the data hub device.

Methods may comprise the further step of communicating the medical treatment parameter to the medical device, followed by the step of sensing a medical treatment parameter during or following the medical treatment, and the step of communicating the medical treatment parameter from the medical device to the data hub device further comprising the step of communicating the sensed medical treatment parameter to the data hub device.

Other embodiments may relate to methods for the transfer of data from a programmable, non-transitory, computer readable storage device to a data hub device comprising the steps of; obtaining a programmable, non-transitory, computer readable storage device wherein the storage device comprises, a substantially non-editable, computer readable program encoding a medical treatment parameter for a medical treatment, obtaining a medical device comprising, a central processing unit, and a storage device reader for receiving the substantially non-editable program, communicating the program to the storage device reader, decoding the medical treatment parameter for a medical treatment from the substantially non-editable program using the central processing unit, conducting the medical treatment in accordance with the set parameters using the medical device, monitoring a medical treatment parameter, communicating data arising from the monitoring of the medical treatment parameter from the medical device to a data hub device, receiving the data transmitted from the medical device at the data hub device, and storing the data at the data hub device or communicating the data from the data hub device to other electronic devices.

The fastener coupling affixed to the computer readable storage device may comprise one or more clips or catches at the perimeter of the fastener coupling. The fastener coupling may be composed of a polymeric material, preferably a moulded plastic or a silicon composite material, and may present in the form of a sliding fastener, a fixed clip or a threaded screw that may be used to secure the computer readable storage device in position. The fastener coupling may be shaped to form a handle or gripping surface to aid the insertion of the computer readable storage device into the space formed within the medical device. It may additionally comprise a surface for printing information relating to the computer readable storage device, for instance, the flow rate of the medical treatment parameter.

A fastener, formed by bringing together corresponding mating portions of the programming key fastener coupling and the medical device fastener coupling, may protect the internal components of the medical device from damage (for example, damage caused by dust or moisture). The fastener may create a seal between the mating portions of the programming key fastener coupling and the medical device fastener coupling. The seal is preferably splash proof, allowing the user to wear the medical device in wet environments, when the programming key is engaged with the medical device.

The medical device is preferably a wearable medical device thus, the exterior surface of the programming key is preferably continuous with the exterior surface of the medical device when the programming key is engaged with the medical device. This may occur, for instance, while inserting the computer readable storage device in the opening within the infusion pump, that receives the computer readable storage device. This creates an aesthetically appealing finish to the medical device, as well as providing comfort to the user.

The fastener coupling of the medical device preferably comprises one or more, tongues, grooves, clips or catches located at the perimeter of the opening. In another form, the fastener coupling at the medical device opening surrounds the perimeter of the opening, for example in embodiments wherein the fastening is a screw and the fastener couplings comprise a male and female threaded portion.

In certain embodiments, the fastener may form a substantially non-releasable fastening. This may render the assemblies or systems described herein substantially non-tamperable. It may help to secure the programming of the medical treatment parameter by ensuring that the encoded medical treatment parameter for the medical treatment cannot be unintentionally ceased or altered by removing the storage device.

A substantially non-releasable fastening may be formed by bringing together fastener couplings comprising substantially non-releasable clips or catches. For example, non-releasable clips or catches may comprise a spring-loaded mechanism, such as a spring-loaded lug fitting within a small aperture, or a tongue and groove.

A substantially non-releasable mating arrangement may be formed between the storage device data connector and the medical device data connector. Such an engagement may also establish a non-tamperable engagement between the programming key and the medical device, presenting an alternative to the non-tamperable feature of the non-releasable fastener couplings.

A substantially non-releasable fastening may also comprise a fracturable or breakable portion of the computer readable storage device. The fastening may be rendered non-releasable by fracturing the fracturable or breakable portion of the computer readable storage device once the storage device has been inserted in the medical device opening, such that the storage device remains stuck in the medical device and cannot be grasped to be removed. The fracturable or breakable portion may be defined by a weakening in the storage device or fastener coupling.

Preferably, the fracturable or breakable portion provides a gripping portion of the computer readable storage device such that it can be manipulated using the gripping portion until the gripping portion is fractured and removed.

The conformation or shape of the fastener coupling may be configured to cover the priming mechanism. Preferably, this form and positioning enable the priming mechanism to remain disengaged until the programming key is mated with the data connector and fastener coupling of the medical device.

In their simplest form, embodiments may comprise a programming key comprising a printed circuit board, a data connector, a storage device and a fastener coupling. In such simple forms, the programming key takes the form of a resistor-based device which simply completes a broken circuit within the medical device. In such simple devices, an external power source is typically not required, as the programmed parameter is passively received by the medical device or may utilise the power source provided by the medical device. However, such infusions are limited in the duration of infusion and the viscosity of the liquid that can be infused.

In certain embodiments of the invention, the fastener coupling may comprise a tongue and groove sliding fastener. Further, the sliding fastener may comprise a substantially planar portion and a tongue or groove portioned formed at one or more edges of the planar portion, wherein the tongue or groove is configured to mate with a corresponding tongue or groove partially defining the space within the medical device.

Embodiments may comprise a substantially planar portion formed of the same material as the medical device, for instance polymeric materials or silicone composite materials. The planar portion may be formed in the shape of a corresponding opening or 'cut-out' through an exterior housing of the medical device. The substantially planar portion and opening are preferably rectangular in shape with two substantially parallel edges of the planar portion having a tongue formed therein. A corresponding pair of substantially parallel grooves may be formed in two substantially parallel edges formed in the opening of the medical device housing. Thus, when the programming key is engaged with the medical device, and the fastener coupling of the programming key is mated with the fastener coupling of the medical device the substantially parallel pair of tongues are brought into sliding engagement with the substantially parallel pair of grooves.

Preferably, a priming sequence or an infusion is initiated once the programming key is engaged with the medical device.

In certain embodiments the sliding fastener may comprise a locking means configured to engage with a corresponding means on the medical device to secure the sliding fastener in position when the data connector and fastener coupling are mated with the corresponding data connector and fastener coupling on the medical device.

For instance, the pair of substantially parallel tongues on the sliding fastener may terminate in a hook corresponding with the pair of substantially parallel grooves on the medical device which terminate in a pair of wider openings, such that, when engaged the terminal hooks are locked in position in the wider openings of the grooves.

Data connectors of some embodiments may comprise a unique data connector configured to impede mating with commonly available data connectors. In particular, such data connectors may be configured to impede mating with USB, micro USB, ethernet ports, HDMI, micro HDMI, modular plugs, modular jacks, or firewire connectors.

In an alternative form, the fastening may comprise a releasable fastening. A releasable fastening may enable the user to vary the medical treatment parameter by removing the computer readable storage device and replacing the computer readable storage device with a further storage device comprising an alternative medical treatment parameter. This will prevent the need for disposal of the medical device, enabling the continued use of the medical device throughout a complex or prolonged infusion treatment.

In certain situations, a medical professional may monitor a patient during a medical treatment, and if the patient is not responding to the treatment as the medical professional had anticipated, the medical professional may seek to alter the medical treatment parameter. This may occur during surgery, during emergency situations or as a result of an accident. In these situations, the medical professional may remove the computer readable storage device comprising the substantially releasable fastening. The medical professional may then obtain an alternative computer readable storage device encoding the desired medical treatment parameter and place it in the medical device.

Where the fastening comprises a substantially releasable fastening, the medical device may be programmed to continue to operate at the programmed medical treatment parameter after the computer readable storage device has been removed, until the alternative computer readable storage device is received by the medical device.

The programmable, non-transitory, computer readable storage device of certain embodiments may encode one or more medical treatment parameters for operating the medical device. However, more than one medical treatment parameters may be encoded on the device.

The computer readable storage device may comprise a digital key. A digital key may be configured to encode any one of a number of instructions for the operation of a medical device. In particular, the digital key may comprise a digital flow key configured to encode a flow rate for the administration of liquid infusions.

A digital flow key is preferably used in combination with an infusion pump. The digital flow key may provide a number of instructions relating to a medical infusion, for example, the flow rate of the infusion, the total volume of the infusion, a sequence for the priming of the infusion pump, a baseline infusion rate or the like.

Alternatively, the priming sequence may be pre-programmed in the infusion pump whereby engagement of the digital flow key may initiate or enable operation of a user priming sequence. For instance, a user priming sequence may comprise the steps of connecting an intravenous bag, activating the infusion pump, pressing and holding a priming button, priming of the line (which may occur over five seconds to remove air from the line, for instance by pumping about 1 ml of fluid through the line), inserting a programming key, and pressing the start button.

More complex embodiments of the programming key may draw auxiliary power or higher voltages. For instance, high viscosity liquids (such as blood products) may require additional power and/or higher voltages to infuse high viscosity liquids at required flow rates. Thus, certain embodiments of the programming key may comprise an auxiliary power source, such as a battery. Such embodiments enable a single use infusion pump to be used for extended infusions and/or for the infusion of viscous liquids.

In some embodiments, priming cannot proceed once the flow key has been inserted into the infusion pump; this may prevent accidental activation by the patient. For instance, an infusion may switch from a priming sequence to an infusion sequence once the flow key has been introduced into the medical device. The maximum limit of priming attempts may be set at, for instance, three attempts.

Preferably, the flow key is pre-programmed to a fixed flow rate. Preferred flow rates comprise 0.5 ml/hour, 1 ml/hour, 2 ml/hour, 4 ml/hour, 5 ml/hour, 10 ml/hour, 20 ml/hour, 25 ml/hour, 40 ml/hour, 50 ml/hour, 60 ml/hour, 75 ml/hour, 80 ml/hour, 100 ml/hour, 120 ml/hour and 150 ml/hour. For typical liquids such rates may be delivered by a resistor-based programming key.

Preferred embodiments may comprise a programming key providing the medical treatment parameter of a flow rate. Such embodiments may be provided as resistor-based programming keys. Typically, programming of multiple parameters may be provided by programming keys comprising an auxiliary power source.

The computer readable storage device may take the form of a memory card, a smart card, an electrically erasable programmable read only memory (EEPROM) tag, a radio frequency identification data (RFID) tag, or a similar portable device comprising an embedded integrated circuit. The computer readable storage device may be encrypted. The computed readable storage device may store any quantity of data deliverable by a suitable compact device.

The programming key may also store a large amount of information about the patient and their treatment such as an authentication key, a security key, a patient's identity, the identity of the drug and diluent being infused, the flow rate of a drug being infused, the volume of the drug being infused, the temperature of the infusion solution, a schedule of the treatment regime for a patient or an instruction manual.

In circumstances where the fastener coupling on the programming key comprises a releasable fastening and the medical device is an infusion pump, the infusion pump may continue to operate at the programmed flow rate after the flow key has been removed. That is, until an alternative flow key encoding a different flow rate is received by the infusion pump. This enables the user to continue using the same bag of fluid containing the medicament.

The infusion pump may preferably receive information, for example sensed information, relating to the volume of fluid that has been infused, the volume of fluid within the bag at the commencement of the infusion, or the remaining volume of fluid in the bag. This information may be entered directly or calculated by the infusion pump based on other parameters. Other sensed parameters, such as temperature of the fluid, may also be communicated back to the infusion pump.

The programming key may comprise an electrically erasable programmable read only memory (EEPROM) device, radio frequency identification data (RFID) tag, a central processing unit (CPU), a memory reader, a card reader, a port connected to a cable or all of the above.

Preferably, the programming key may be used to store confidential data such as an authentication key, a security key, a patient's identity, an access rule reference, a doctor or nurse's identity, the patient's infusion and/or administrative data, the infusion flow rate, the volume of infusion, a schedule and setting information. An EEPROM may also comprise a RFID tag to process, store and monitor the drug to be infused, infusion flow rates, temperature of the drug, and the like.

The programming key is preferably pre-programmed. The flow rate is preferably pre-programmed during manufacture of the programming key. Preferably, the flow rate is programmed such that it is decipherable by an infusion pump. The flow rate may be tested during the manufacturing process to ensure the accuracy of the flow rate and/or to ensure that the flow rate has been rendered non-editable. The programming key may be pre-programmed to have a fixed flow rate such as 0.5 ml/hour, 1 ml/hour, and so on, to avoid any overdosing or underdosing. The programming key may be disposed of after use and a new programming key may be used for a further infusion.

In another form, the computer readable storage device may further comprise a port or a cable to form an electronic connection with a second storage device, a data hub device, a battery charger or to communicate or transfer the data received from the first storage device. The second storage device may be present in the form of sim card, an electrically erasable programmable read only memory (EEPROM) device, radio frequency identification data (RFID) tag, a central processing unit (CPU), a memory reader, a card reader, a wireless connection and the like.

The computer readable storage device may store a computer readable program encoding the information or data describing a medical treatment. The computer readable storage device may also encode a unique identifier. The unique identifier is preferably applied during the manufacturing of the computer readable storage device. The unique identifier may identify the authenticity of the computer readable storage device and/or it may identify the make, model or other information relating to the computer readable storage device. The unique identifier may be read by the medical device as a further safety measure to ensure the computer readable storage device encodes an authentic medical treatment or a treatment approved by a drug library.

In a further embodiment, the unique identifier of the computer readable storage device may be communicated to the data hub. The data hub may undertake one or more further safety measures. For instance, it may match a sensed flow rate with the flow rate applied to the unique identifier during manufacture. This also provides a further quality assurance measure to identify any product failures. Also, any counterfeit products may be identified, located and destroyed.

In one form of the invention, the process of transferring the information relating to the treatment via a computer readable storage device may be unidirectional. Unidirectional data flow may secure the data, in particular by ensuring that the data cannot be overwritten.

In certain embodiments it is envisaged that while the information relating to the treatment may be unidirectional, other information transferred between the computer readable storage device and the medical device may be communicated bidirectionally. It is envisaged, also that data may be added to the computer readable storage device without overwriting the program, via secure mechanisms commonly known to those skilled in the art.

The substantially non-editable, computer readable program may be secured for accidental or deliberate tampering by encryption of the program. In such instances, the encrypted program may be decoded by the medical device. Alternatively, decryption may be carried out by a second program located on the computer readable storage device which is triggered when the computer readable storage device is connected with or brought into contact with the medical device or the data hub.

Embodiments comprising the medical device may take the form of an infusion pump, a dialysis machine or any other medical device that can deliver a drug or blood product into a patient's body at a prescribed rate and volume over a certain period.

The medical device may comprise an opening adapted to receive the computer readable storage device affixed to a fastener coupling. Preferably, the opening may take the form of a mounting cavity within which the computer readable storage device may be inserted. The mounting cavity may comprise a locking mechanism such as a sliding fastener, a clip, a screw or a sliding lock to slide and optionally lock the computer readable storage device into the mounting cavity. This preferably prevents the removal or tampering of the computer readable storage device.

In one embodiment, the space formed within the medical device may be partially occupied by a storage device reader. The storage device reader may be positioned to contact the computer readable storage device when the storage device is placed within the space formed within the medical device. The storage device reader may read the encoded data or information (which may be the treatment parameter for a patient) stored in the computer readable storage device. The storage device reader comprises a bar code reader, an optical character recognition device, a laser, an RFID antenna, a reader circuit and the like. The reader reads the information encoded on the computer readable storage device which may be decoded and received by the central processing unit (CPU) within the medical device.

The reader may be a bar code reader, an optical character recognition device, a laser, an RFID antenna, a radio communication receiver or a reader circuit. An infusion pump may have one or several readers to receive information from one or more programming keys.

The information decoded by the central processing unit of the infusion pump may be transferred, received or stored. This may take place via a cabled, wireless or other data connection to a data hub device.

The data hub device may comprise a medical device hub or an infusion pump hub. The device may further comprise a central processing unit (CPU), a port to form a cabled connection with another electronic device, componentry capable of establishing at least one form of wireless connectivity (e.g. to establish a Bluetooth, Wifi or other communication signal) to communicate with the medical device.

Other electronic devices may comprise medical devices, a cloud server, an external computer or a smart device. The connection may be configured to ensure the unidirectional transfer of data, for instance, from the medical device to the data hub device. This may be preferred to ensure the security or safety of the medical device. However, the connection may also be configured to permit two way data transfer. This may be preferred where the data hub receives data from multiple devices or sensors. The data hub may aggregate and processes data, in particular complex data or data from multiple sources, for display on a smart device, for feedback to the medical device, or for monitoring by health monitoring services.

Sensors may be integrated into the medical device, an infusion line, an infusion bag or the data hub device to detect any one of a number of parameters, for instance sensors may detect infectious agent (for aseptic condition compliance), they may perform a rapid identification of a medication or rapid identification of the concentration of medication.

In another preferred form, the data hub device may be pre-programmed to display the time and location.

Embodiments wherein the programming key is coupled with the data hub preferably enable the programming key to be written. A program parameter may be written onto a key for setting an infusion administration for an infusion device. Typically, the data hub will collect programmed and/or sensed data generated through the use of the infusion device. The coupled hub and programming key may provide feedback to the medical device on sensed parameters during the infusion.

The medical device hub may comprise a programming key that makes physical contact with the medical device. Alternatively, it can be located elsewhere (either within the medical device or external to the medical device) and may be connected to the medical device via a cabled or wireless network.

In one form, the data hub device may comprise a writable compact disc, or an optical disc such as a CD or DVD, zip drives, USB flash drives or any other magnetic storage device, or another flow key. The second flow key may receive or store the output command such as volume of the drug used or left during or after an infusion, the temperature at the time of infusion or the remaining volume of gas for the infusion or the like.

In another form, the data hub device may comprise a smart device such as a mobile phone, a smart watch, smart headphones etcetera. The smart device may comprise an opening to receive a cable plug connected to the medical device, and a central processing unit (CPU) for receiving and storing the information from the central processing unit (CPU) present within the medical device.

Preferably, the smart device may be connected via a wireless network, such as Bluetooth or Wifi, for receiving and storing information from the central processing unit (CPU) within the medical device. Wireless connectivity may eliminate the need for a cable that may interfere with the patient's care. It may also provide for mobile connectivity solutions for hospitals and outpatient care.

Preferably, the data hub is coupled with the programming key and is wirelessly connected to a server, computer or router. Wireless connectivity may enable the downloading of data collected during the treatment of a patient and/or transportation of a patient during emergency treatment.

Wireless connectivity may offer greater data transmission rates, data streaming connectivity, and a common interface for smart devices such as mobile phones or tablets. These devices may monitor a patient's basic activities and can alert the user to changes in the expected medical treatment parameter. Wireless may further monitor various sensors such as proximity sensing, weight, heart rate, blood pressure, glucose, and so on, allowing remote caregivers or family members to monitor the patient's basic activities and/or medical administration. Proximity sensors may monitor the location of a patient, for instance in cases where patients may happen to wander outside of the home environment. The weight sensor for a patient may monitor food intake and fluid retention.

The data hub may be used to aggregate medical device data in a specific area. Such devices are preferably not wearable but may be located in a monitoring station. For instance, they may cover a geography such as a home, a residential care facility, or a ward in a hospital. This may enable a carer to monitor a patient such that the carer receives alarms and other information relating to the medical treatment (or any other sensed data triggered by the wireless sensor).

A data hub device may comprise a master data hub and a slave. This configuration may offer advantages where a division of alarms, alerts and data flows are required between patients and their carers; whether they are medical practitioners, third party monitoring facilities or family members. For instance, in certain circumstance remote monitoring by a medical professional may be required for patients receiving complex treatments. Alternatively, alarms and alerts may frighten or trigger adverse events for dementia patients (or they may simply be ignored) so alarms may be diverted or repeated to carers.

A master data hub may be located at a monitoring station and the slave may be a wearable held by the patient or a carer. The master data hub may be located in the home, at a residential care facility, in the ward of a hospital or at a third party monitoring facility. The master data hub may be located on a physical network connected to the slave via a cabled connection (for example ethernet cabling), it may be connected to the slave via a local wireless network, or it may be connected to the slave via a cellular network. In certain embodiments, the master data hub may form a cloud based service, which may be particularly advantageous if a carer, medical practitioner or monitoring facility is not co-located with the patient.

The hub may be carried in a carrier, for example a carrier bag or strap. It may be stored, secured and/or protected in a housing, for instance a bag or safety pouch. The safety pouch may comprise a belt or a band, one or more storage sections, optionally with a safety zip to ensure the safety of the components. A band, independent of or combined with a safety pouch, could be used to tie and secure the safety pouch around the waist or arm of the patient so that infusion may be conducted anywhere within the hospital or even at home.

In another form, the carrier, housing or safety pouch may comprise a socket to connect to a cable plug or a connecting port to connect the medical device and the data hub device via a cabled connection. The carrier, housing, or safety pouch may also comprise a cabled or wireless connection with a patient controlled analgesia (PCA) button to call for a medical professional in case of an emergency.

The carrier, housing or safety pouch may store both the infusion pump and the infusion pump hub. The infusion may be carried out into the patient's body even when the components are present in the safety pouch. The data output may be received by connecting the infusion pump and infusion pump hub via a cable.

The invention now will be described with reference to the accompanying drawings together with the examples and the preferred embodiments disclosed in the detailed description.

The invention may be embodied in many different forms and should not be construed as limited to the embodiments described herein. These embodiments are provided by way of illustration only such that this disclosure will be thorough, complete and will convey the full scope and breadth of the invention.

DETAILED DESCRIPTION

EXAMPLES

Figure 1A:
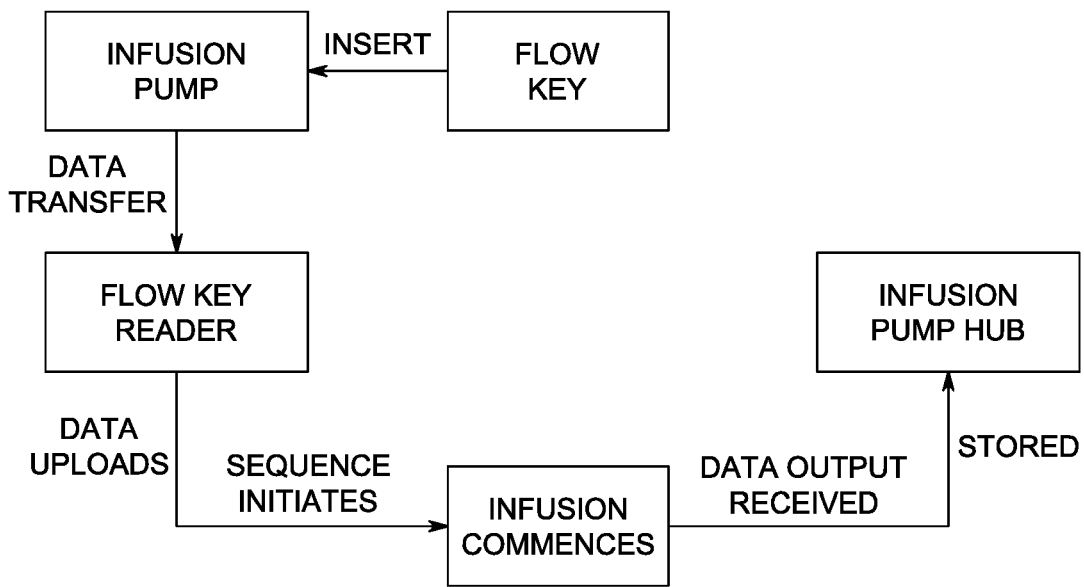
FIG. 1a provides a detailed flow diagram showing the transfer of data from the infusion pump to the infusion pump hub.

Several embodiments of the assemblies, systems and methods according to the invention are described in the following examples. The embodiments described herein have been illustrated by way of data flows involving medical devices such as infusion pumps, and data storage componentry. Thus, the following embodiments are exemplary in nature only and are not intended to be limited to execution using the exemplified hardware or components.

Example 1—Data Flow Model

Data Flow Model for Medical Devices

A programming key is a portable storage device carrying a computer readable program providing instructions for the operation of a medical device. The programming key is typically non-editable to maintain a unidirectional flow of data from the programming key to the medical device, when required to maintain patient safety. The programming key is physically transferred to the medical device providing an interface with the electronic componentry of the medical device. The medical device comprises corresponding electronic componentry to receive the program from the portable storage device and to decipher the operating instructions for the medical device.

The data generated during the operation of the medical device (for instance, records relating to the treatment delivered, parameters sensed by the medical device or the like) is transferred to the medical device hub where it is then stored. In certain embodiments of the invention the medical device hub may be coupled with the medical device to augment the functioning of the medical device. For instance, the medical device hub may sense and record the temperature of the treatment delivered, it may provide capacity for recharging the fuel source of the medical device or it may process data locally for communicating to other devices. The medical device hub may receive or transfer data as a real-time process or as a batch process.

The medical device hub comprises a data store together with the corresponding electronic components to enable the transfer of data from the medical device; to augment the functioning of the medical device and to transfer stored data to another device.

In an alternative embodiment, the programming key forms a component of the medical device hub. The data flow model for such embodiments does not necessitate unidirectional data flows as mentioned above. Further, the physical form of the medical device hub and programming key is altered. For instance, the programming key may be connected to the medical device hub prior to use and thereafter removed and physically placed within the medical device for use. Alternatively, the programming key may be embedded in or connected to the medical device hub whereby communication and data transfer to the medical device is established via a cabled or wireless connection. In this instance, data flows from the programming key to the medical device hub via the medical device may be transferred in two directions.

Data Flow Model for Infusion Pumps

In the embodiments of the invention wherein the medical device is an infusion pump, the programming key is a flow key providing a medical treatment parameter for a medical treatment. The infusion pump receives parameters relating to the medical treatment parameter (for example the flow rate of administration of the treatment); and it performs an infusion in accordance with the medical treatment parameter. The infusion pump hub receives data from the infusion pump on parameters that reflect the actual treatment performed on the patient. The infusion pump hub stores the infusion history and transfers the data captured in batch form to another device. The data flow in this instance is unidirectional therefore, the pre-programmed data cannot be deleted or overwritten but a log data can be written if any changes are required in the treatment regime of the patient.

Data Sequence for an Infusion Pump Hub

A detailed data flow sequence for an infusion pump is shown in FIG. 1a. Individual infusion pump flow keys are pre-programmed to 0.5 ml/hour, 1 ml/hour, 2 ml/hour, 5 ml/hour, 10 ml/hour and 20 ml/hour. The user selects a flow key of the desired flow rate and an infusion pump described according to PCT/AU2017/050019. The flow key is inserted into the infusion pump housing and locked in place to prevent removal and tampering of the flow key. An opening or 'cut-out' in the wall of the infusion pump forms a mounting cavity to receive the flow key. The periphery of the mounting cavity comprises a locking mechanism or a sliding lock to slide the flow key into the mounting cavity.

The flow key mounting cavity is formed adjacent to a flow key reader built into the infusion pump, to read the data input from the flow key. The input data is then uploaded to the infusion pump's CPU and the infusion sequence is initiated. Once the sequence is initiated, the infusion commences into the patient's body. The data output is then received and stored in the infusion pump hub. The data output is received and stored in the infusion pump hub.

The infusion process may be administered by a medical professional, carer or it may be self-administered.

Example 2—User Journey

Figure 1B:
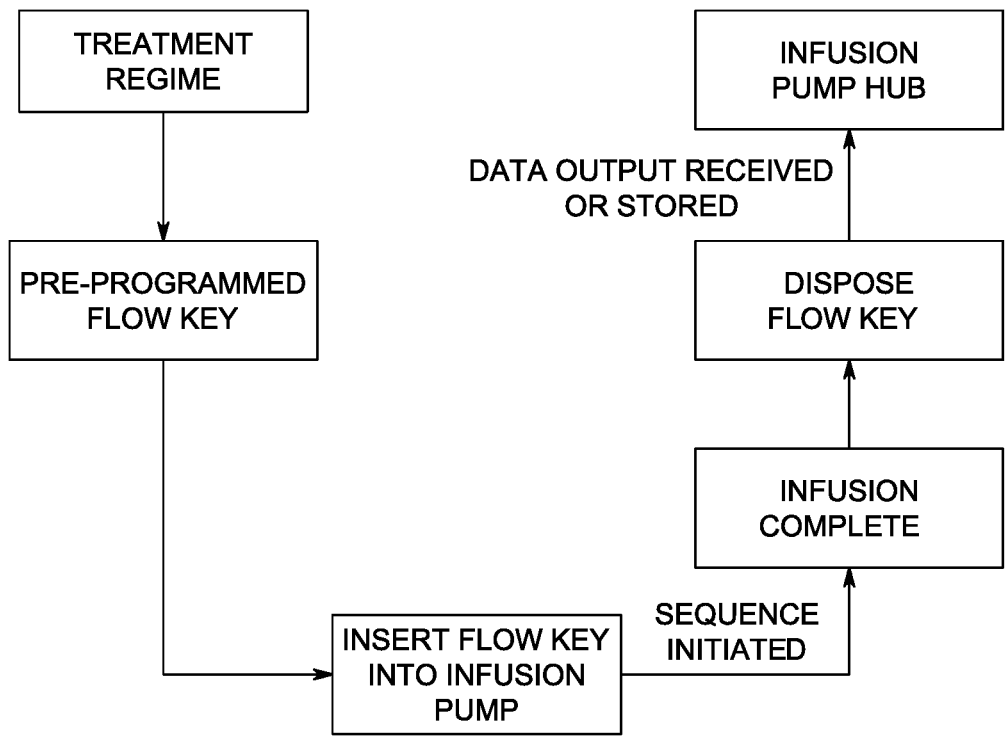
FIG. 1b provides a detailed flow diagram showing the transfer of data across the user journey; from the infusion pump to the infusion pump hub.

FIG. 1b shows a user journey for embodiments of the invention involving a pre-determined pharmaceutical treatment regime. With reference to FIG. 1b, the user selects a treatment regime as prescribed by a medical professional. The user obtains a pre-sterilised and pre-programmed flow key set to the prescribed flow rate desired for the drug being infused into the patient's body, and a pre-sterilised infusion pump (described in PCT/AU2017/050019).

The user obtains all other necessary materials and equipment for performing the desired infusion (for example, picc line, leur lock fitting, sterile swabs, intravenous bag and the like) and prepares the patient to receive a picc line in accordance with clinically accepted aseptic techniques, commonly known to persons skilled in the art.

The patient, infusion bag and infusion pump are then prepared for the infusion in accordance with local clinical practice.

The user activates the infusion pump and initiates the priming sequence by pressing and holding the priming button on the infusion device. The line is primed by pumping about 1 ml of fluid through the line over five seconds to remove air from the line.

The flow key is inserted into the infusion pump to transfer the data relating to the treatment regime, which also activates the infusion pump. Once the pump is initiated, an administration sequence is initiated to administer the patient's treatment regime pre-set in the flow key described above.

Once the infusion is complete, the flow key and infusion pump are disposed of and the output data is received and stored in the infusion pump hub.

The infusion pump hub can be used for an extended infusion in cases where the pre-set flow key completes the infusion and a further infusion is required for an extended period of time. The infusion pump hub can be pre-programmed to display the time and location.

In this example, the embodiment of the invention ensures a safe mechanism for administering a predetermined infusion treatment and recording a patient's infusion history.

Example 3—Infusion Pump Programming Assembly

Figure 2A:
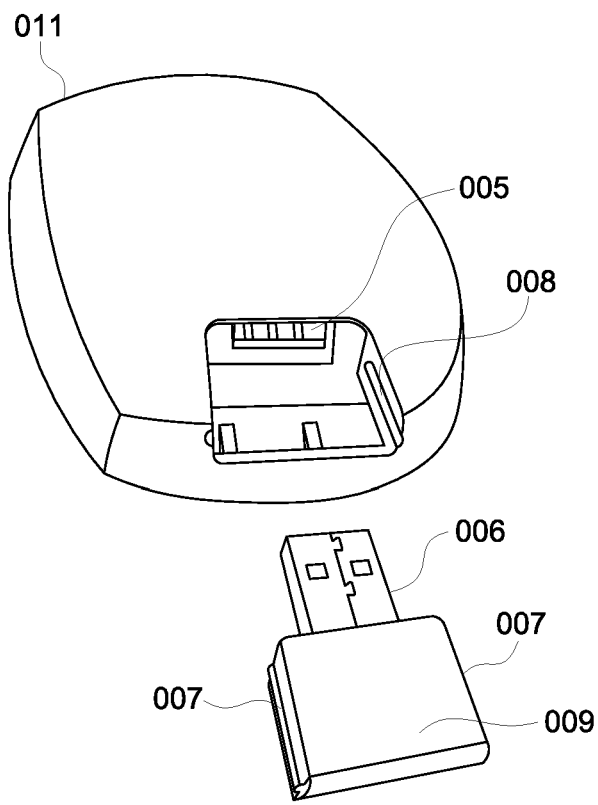
FIGS. 2a and 2b illustrate an infusion pump programming assembly according to embodiments of the invention; including a flow key and an infusion pump.

FIG. 2a shows an infusion pump programming assembly comprising an infusion pump 011 and a sliding fastener 009 wherein the infusion pump 011 defines a planar shell-like structure with a small opening moulded onto the upper portion of the infusion pump 011 for receiving a sliding fastener 009.

The opening comprises a pair of grooves 008 to hold the fastener 009 in place. The grooves 008 are located at opposite lengthwise edges of the opening parallel to one another. The opening may also comprise a data connector 005 for forming a connection with a data connector on a flow key 006.

Figure 2B:
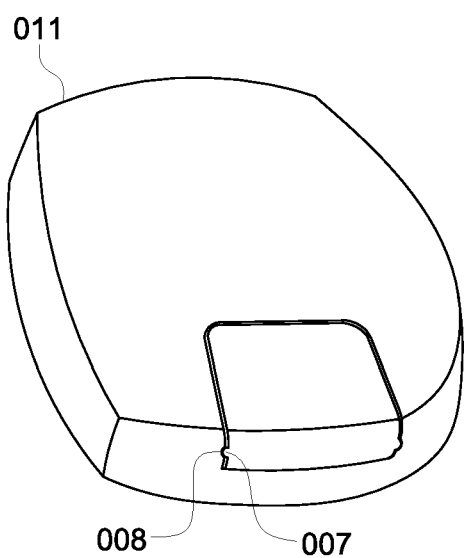

The fastener 009 is formed of a planar cover moulded with the same material forming the infusion pump shell. The outer perimeter of the fastener comprises a pair of tongues 007 at opposite lengthwise edges of the fastener 009 wherein the tongues 007 are formed to slide into the grooves 008 of the infusion pump opening. The tongue 007 on the fastener 009 may terminate in a hook to correspond with an enlargement of the groove 008 formed at the end of the groove 008 in the infusion pump 011 as shown in FIG. 2b. In certain embodiments, this may be formed to render the infusion pump 011 a single use device; thereby avoiding safety issues arising from reprogramming errors.

As shown in FIG. 2a, the fastener 009 comprises a programming flow key 006 which is a unique connector, formed to impede connection with other commonly known data connectors such as USB, micro USB, ethernet ports, HDMI, micro HDMI, modular plugs, modular jacks, firewire connectors and so on.

The flow key 006 comprises a pair of internal, curved, resistant flanges (not shown) to provide a locking mechanism to lock the flow key 006 into the opening of the infusion pump 011. The size and shape of the flow key 006 is formed such that the flow key 006 slides into the opening and locks well when the fastener slides within the grooves 008, forming a connection with the data connector 005. Once the flow key 006 is connected, the fastener 009 completes the exterior of the infusion pump and forms a smooth finish as shown in FIG. 2b.

Example 4—Infusion Pump Hub Assembly

Cabled Assembly

Figure 3:
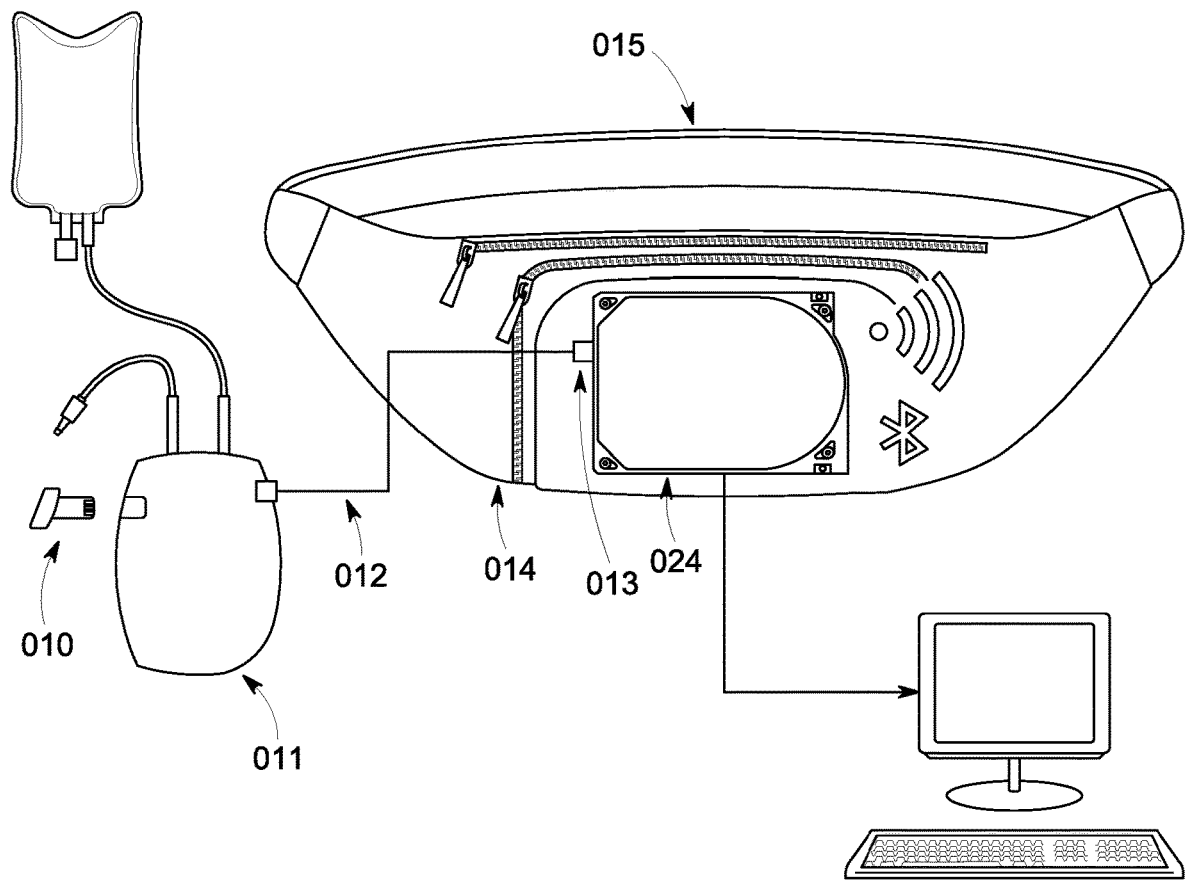
FIG. 3 shows a cabled data transfer system between an infusion device and a data hub.

FIG. 3 shows a cabled system comprising a pre-programmed flow key 010 which is inserted in the infusion pump 011 to transfer data from the infusion pump 011 to the infusion pump hub 024. The infusion pump 011, in this example, further comprises a fixed cable 012 to connect to the infusion pump hub 024. The infusion pump hub 024 comprises a standard data port 013 that connects to the fixed cable 012 of the infusion pump 011, and a CPU that receives and stores the output data. In one embodiment, the infusion pump hub 024 mentioned above is protected in a safety pouch 014.

The safety pouch 014 comprises a belt or band 015, two padded storage sections along with a safety zip to maintain the safety of the components. The band 015 of the safety pouch 014 can be used to tie and secure the safety pouch 014 around the waist or arm of the patient so that an infusion can be conducted anywhere; within the hospital or even in home. The safety pouch 014 can also house a thermometer to measure the infusion temperature of the treatment, a pressure sensor to sense the volume of solution infused into the patient and the rate of infusion, and a recharging station to recharge the infusion pump energy source.

In another form of this example, the safety pouch 014 can store both the infusion pump 011 and the infusion pump hub 024 (not shown), such that the infusion can be carried out into the patient's body even when the components are present in the safety pouch 014.

The data output from the infusion pump 011 (and any additional sensors and devices external to the infusion pump 011) is received by the infusion pump hub 024 by connecting the infusion pump 011 and infusion pump hub 024 via a cable 012. In this example, the embodiment of present invention ensures the safety of the components. This is particularly useful if the patient wishes to receive the infusion at home or in hospital.

Cabled Pump Ports

Figure 4A:
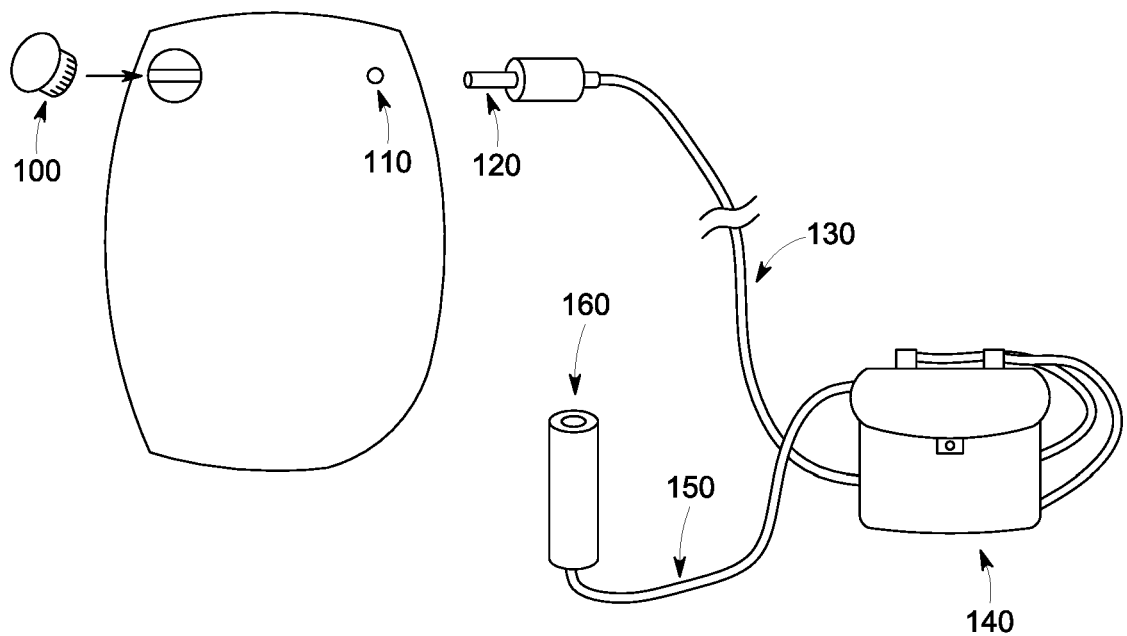
FIG. 4a illustrates embodiments including a cabled data transfer system from the infusion pump to the data hub, via cabled ports.

FIG. 4a shows an infusion pump comprising a reader to receive a pre-programmed flow key 100. The infusion pump further comprises a port or socket 110 to receive a cable plug 120 connected to the safety pouch 140 via cable 130. The safety pouch comprises an infusion pump hub and a CPU (not shown) to receive and store the data output. A patient controlled analgesia (PCA) button 160 is connected to the safety pouch 140 via a second cable 150 to call or alarm the medical professional or use in case of an emergency.

Figure 4B:
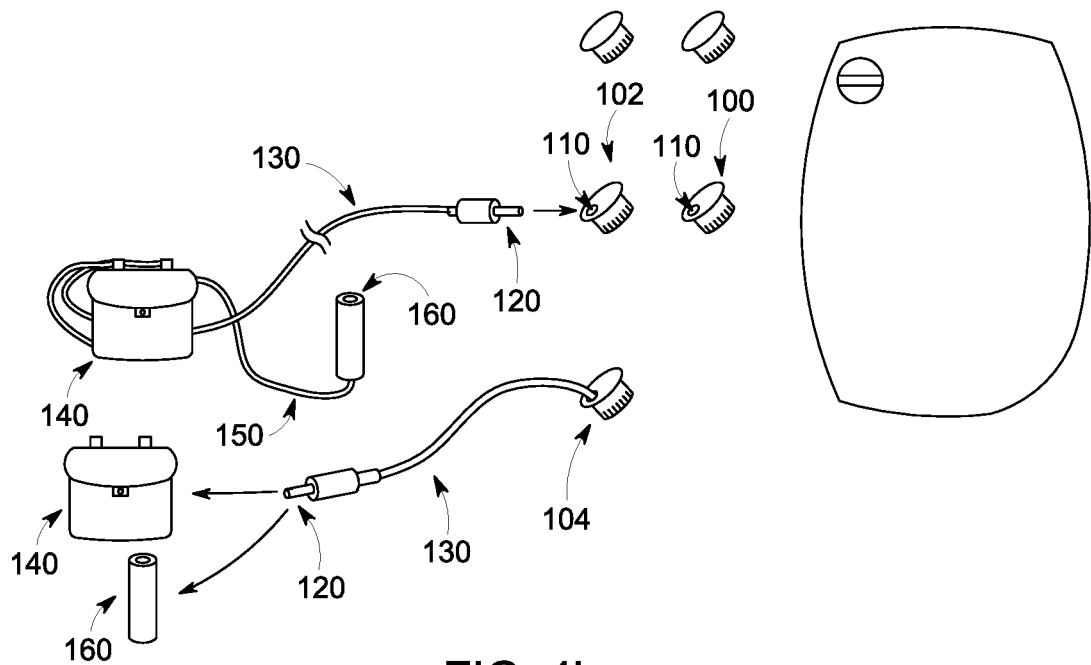
FIG. 4b illustrates different types of flow keys for cabled data transfer from the flow key to the data hub.

Different forms of the flow key are shown in FIG. 4b. In one form, the flow key 102 has a socket 110 to connect to a cable plug 120. The cable plug 120 is further connected to an infusion pump hub secured in the safety pouch 140 and the PCA button 160. The socket 110 on the flow key 102 is splash proof to avoid significant damage. This flow key 102 is then inserted into the infusion pump and brought into contact with the reader of the infusion pump to initiate and carry out the infusion. The data may then be received and stored in the infusion pump hub.

The infusion pump hub may include a headphone socket comprising a fixed cable. This embodiment of the invention allows the patient to perform multiple tasks at the same time to receive an infusion, transfer the data input, receive and store data output, and to access a PCA button 160.

In another form, the flow key 104 has a fixed cable 130 with a cable plug 120 at the free end. The cable plug 120 is connected to the safety pouch 140 or a PCA button 160. The infusion may be commenced once the flow key 104 is inserted into the infusion pump and brought into contact with the flow key reader of the infusion pump. This embodiment also allows multiple tasks to be performed at the same time; such as receiving an infusion, transferring the data input, receiving and storing data output, and maintaining access to a PCA button 160.

Wireless Assembly

Figure 5:
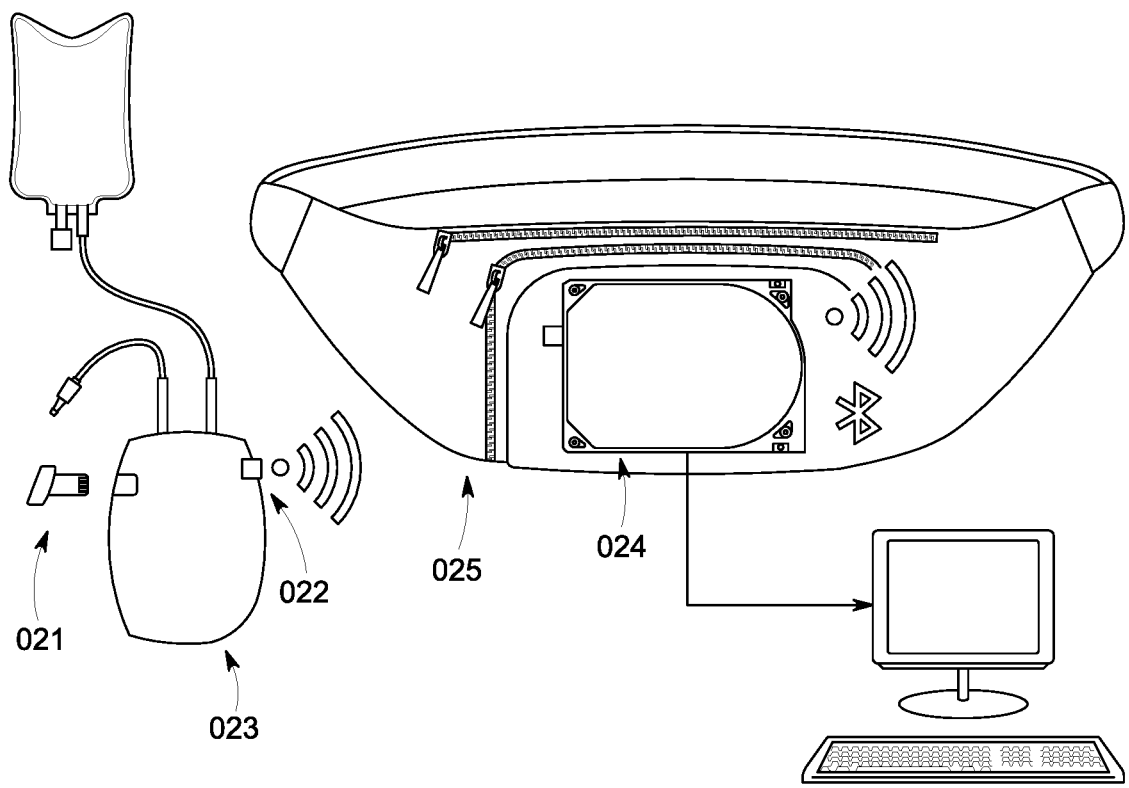
FIG. 5 illustrates a wireless system for data transfer from the infusion device to the data hub.

In wireless embodiments of the invention illustrated in FIG. 5, the infusion pump may receive the flow key which is then brought into contact with the infusion pump reader. A wireless connection 022, such as a Wifi connection, may be established between the infusion pump 023 and the infusion pump hub 024 to transfer data from the infusion pump 023 to the infusion pump hub 024. In this case, the data input is transferred by the flow key 021 and the data output is transferred via wireless 022 to the infusion pump hub 024.

The infusion pump hub 024 may then share the data to other devices via a cable or wireless signal such as a Bluetooth or WiFi signal. Wireless communication is preferred for sharing data with smart devices and wearables such as smart watches, mobile phones or the like, which connect to wireless networks and carry a wireless receiver. In this form of the invention, the infusion pump hub 024 is stored in the safety pouch 025.

In another form of the present invention, both the infusion pump 023 and the infusion pump hub 024 are placed in the safety pouch 025, and data is shared via wireless connectivity (not shown).

Additional functional features may be present in the safety pouch, for instance, a magnetic clasp may be integrated into the safety pouch to ensure the secure connection of the infusion pump 023 and the infusion pump hub 024 to the safety pouch 025. The safety pouch 025 may comprise a reader to establish a contactless connection via Bluetooth or Wifi.

The safety pouch 025 can also comprise a magnetic flow key to ensure a contactless connection with the reader. Thus, physical contact between the flow key and reader is not essential for the above-mentioned embodiments of the present invention to have full effect.

The safety pouch 025 has a belt or bands to keep the infusion pump 023 and infusion pump hub 024 close to the patient's body to allow for a controlled and effective infusion, and a fast transfer of data. The safety pouch 025 can be tied around the waist of a patient's body or the arm of a patient. The safety pouch 025 can also comprise a hook to safely secure the safety pouch 025 on clothes such as shirt pockets, pants etc of the patient.

Wireless Pump Ports

Figure 6:
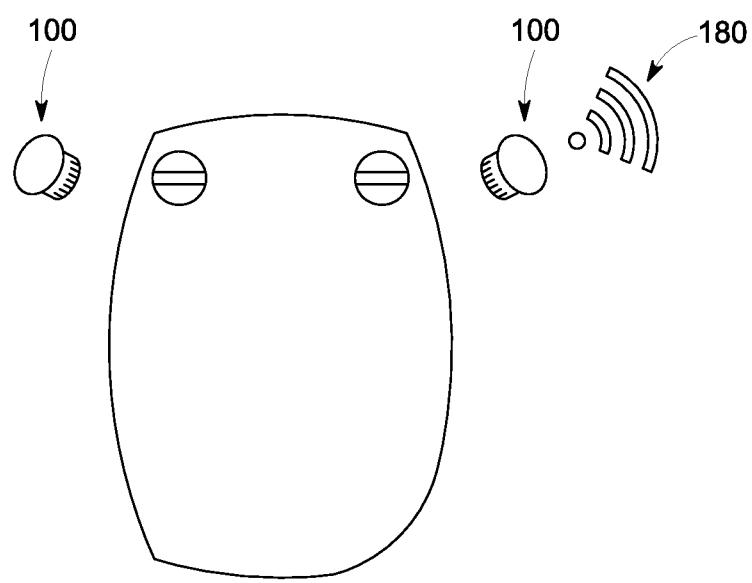
FIG. 6 shows a flow key having a wireless connection for data transfer.

FIG. 6 illustrates an infusion pump configured to operate in a wireless environment. The infusion pump comprises an opening to receive the pre-programmed flow key 100 for transferring data sensed during treatment. A port within the infusion pump is further configured to receive a Wifi antenna 180 (in the form of screw-in aerial) configured to transfer the output data to the infusion pump hub. In this form of the example, the infusion pump hub has corresponding wireless componentry to receive and store the data output over a wireless network. The infusion pump hub may in turn connect to a smart phone or smart watch.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

While the invention has been described above in terms of specific embodiments, it is to be understood that the invention is not limited to these disclosed embodiments. Upon reading the teachings of this disclosure many modifications and other embodiments of the invention will come to the mind of those skilled in the art to which this invention pertains, and which are intended to be and are covered by both this disclosure and the appended claims.

It is indeed intended that the scope of the invention should be determined by proper interpretation and construction of the appended claims and their legal equivalents, as understood by those skilled in the art relying upon the disclosure in this specification and the attached drawings.

LIST OF REFERENCES

United States Food and Drug Administration (2010) White Paper: Infusion Pump Improvement Initiative; http://www.fda.gov/medicaldevices/productsandmedicalprocedures/GeneralHospitalDevic esandSupplies/Infusion-Pumps/ucm205424.htm#types.

Mizuuchi, M. and A. Namiki (2003) *The infusion rate of most disposable, non-electric infusion pumps decreases under hypobaric conditions*, Can J Anesth 7 (50).

Grissinger, M. (2013) *Improved Safety Needed in Handling Elastomeric Reservoir Balls Used for Pain Relief*, Medication Errors, Vol. 38 No. 5, May 2013.

Irish Medicines Board (2008) *Disposable Infusion Devices IMB Safety Notice: SN2008(06) Medical Device Safety Notice*.

Reston, J. (2013) *Making Health Care Safer II: An Updated Critical Analysis of the Evidence for Patient Safety Practices, Chapter 6. Smart Pumps and Other Protocols for Infusion Pumps: Brief Review (NEW)*, AHRQ Publication No. 13-E001-EF, No. 211, March 2013.

Kaye, R., and Crowley, J. (2000). *Medical device use-safety: Incorporating human factors engineering into risk management*, Food and Drug Administration, Center for Devices and Radiological Health. Washington, DC: U.S. Department of Health and Human Services.

ISMP (2007). *Fluorouracil error ends tragically, but application of lessons learned will save lives*, Medication Safety Alert. 12: 1-4.

The invention claimed is:

1. A medical device programming assembly for programming a medical treatment parameter on an infusion device configured to receive a programming key, the medical device programming assembly comprising:
  a programming key configured to mate with the infusion device, the programming key further comprising:
    a cover for supporting one or more programming key components, the components comprising:
      a programmable, non-transitory, computer readable storage device affixed to the cover and encoding a digital key, a priming sequence and one or more medical treatment parameters for operating the infusion device;
      a data connector electrically connected to the storage device and configured to mate with a corresponding data connector on the infusion device for the transfer of data from the storage device to the infusion device; and
      a fastener coupling providing a locking means, the fastener coupling affixed to the storage device and configured to mate with a corresponding coupling on the infusion device when the data connector is connected with the corresponding data connector on the infusion device;
  wherein the programming key storage device is configured to occupy a shape formed by the infusion device, and the locking means is configured to lock the cover and the infusion device when the programming key data connector and fastener coupling are mated with the corresponding data connector and fastener coupling on the infusion device.

2. A medical device programming assembly according to claim 1 wherein the fastener coupling comprises a tongue and groove sliding fastener, and the cover further comprises a substantially planar portion configured to cover the shape formed within the infusion device, terminating in a tongue or groove portion formed at one or more edges of the substantially planar portion configured to mate with a corresponding tongue or groove partially defining the shape within the infusion device, and the locking means configured to engage with a corresponding means on the infusion device to secure the tongue and groove sliding fastener in position when the data connector and fastener coupling are mated with the corresponding data connector and fastener coupling on the infusion device.

3. A medical device programming assembly according to claim 1 wherein the data connector comprises:
  a unique data connector configured to impede mating with commonly available data connectors; and
  a fastener coupling configured to mate with a corresponding coupling on the infusion device and configured to form a non-releasable locking means between the storage device data connector and the infusion device data connector and thereby a non-tamperable engagement between the programming key and the infusion device.

4. A medical device programming assembly according to claim 1, the medical device programming assembly comprising:
  a data hub device adapted to:
    receive data transmitted from the infusion device;
    receive data including the one or more medical treatment parameters for operating the infusion device, encoded by the programmable, non-transitory, computer readable storage device;
    store the data; and process the data, display the data or communicate the data to the same or another electronic device.

5. A medical device programming assembly according to claim 4 wherein the data hub device comprises a server or a router for communicating the data including the one or more medical treatment parameters for operating the infusion device to another electronic device.

6. A medical device programming assembly according to claim 4, wherein the data hub device is configured to encode the digital key, the priming sequence and the one or more medical treatment parameters for operating the infusion device to the programmable, non-transitory, computer readable storage device of the infusion device.

7. A medical device programming assembly according to claim 1, the medical device programming assembly comprising:
a central processing unit, and an infusion device comprising:
a fastener coupling configured to mate with a corresponding coupling on the programming key; and
a storage device reader comprising a data connector configured to mate with a corresponding data connector on the programming key;
wherein the infusion device is configured to define a shape for receiving the programming key when the data connector and fastener coupling on the infusion device are mated with the corresponding data connector and fastener coupling of the programming key.

8. A medical device programming assembly according to claim 7 wherein the infusion device is configured to be activated when the data connector is connected with the corresponding data connector on the programming key.

9. A method of manufacturing a medical device programming assembly according to claim 1.

10. A method of manufacturing a medical device programming assembly according to claim 1 wherein the method comprises the steps of:
obtaining a programmable, non-transitory, computer readable storage device comprising a data connector wherein the data connector is configured to mate with a corresponding data connector on the infusion device;
programming the programmable, non-transitory, computer readable storage device to encode a digital key, a priming sequence and one or more medical treatment parameters for operating the infusion device; and
affixing the storage device to a fastener coupling providing a locking means and being configured to mate with a corresponding coupling on the infusion device when the data connector is connected with the corresponding data connector on the infusion device.

11. A method of manufacturing a medical device programming assembly according to claim 10 wherein the step of programming the programmable, non-transitory, computer readable storage device comprises the additional step of rendering the medical treatment parameter substantially non-editable.

12. A medical device programming assembly according to claim 1 wherein the conformation or shape of the fastener coupling is configured to cover a priming mechanism of the infusion device, to form a non-tamperable engagement between the programming key and the infusion device, and to enable the operation of the priming sequence upon engagement of the programming key with the infusion device.

13. A system for programming a medical treatment parameter on an infusion device configured to receive a programming key, the system for programming a medical treatment parameter comprising:
a programming key adapted to mate with the infusion device, the programming key further comprising:
a cover for supporting programming key components, the components comprising:
a programmable, non-transitory, computer readable storage device affixed to the cover encoding a digital key, a priming sequence and one or more medical treatment parameters for operating the infusion device;
a data connector electrically connected to the storage device and configured to mate with a corresponding data connector on the infusion device for the transfer of data from the storage device to the infusion device; and
a fastener coupling providing a locking means affixed to the storage device and configured to mate with a corresponding coupling on the infusion device when the data connector is connected with the corresponding data connector on the medical device;
wherein the programming key storage device is configured to occupy a shape formed by the infusion device and the locking means is configured to lock the cover and the infusion device when the data connector and fastener coupling are mated with the corresponding data connector and fastener coupling on the infusion device.

14. The system for programming a medical treatment parameter according to of claim 13 comprising:
a data hub device adapted to:
receive data transmitted from the infusion device;
receive data including the digital key, the priming sequence and the one or more medical treatment parameters for operating the infusion device, encoded by the programmable, non-transitory, computer readable storage device;
store the data; and
process the data, display the data or communicate the data to the same or another electronic device.

15. The system for programming a medical treatment parameter according to claim 13 comprising:
a central processing unit, and
an infusion device comprising:
a fastener coupling configured to mate with a corresponding coupling on the programming key; and
a storage device reader comprising a data connector configured to make with a corresponding data connector on the programming key;
wherein the infusion device is configured to define a shape for receiving the programming key when the data connector and fastener coupling on the infusion device are mated with the corresponding data connector and fastener coupling of the programming key.

16. A method for the transfer of data from a programmable, non-transitory, computer readable storage device to a data hub device comprising the steps of:
obtaining a programming key further comprising:
a cover for supporting one or more programming key components;
a programmable, non-transitory, computer readable storage device affixed to the cover and encoding a digital key, a priming sequence and a medical treatment parameter for operating an infusion device;
a data connector electrically connected to the storage device and configured to mate with a corresponding data connector on the infusion device for the transfer of data from the storage device to the infusion device; and a fastener coupling providing a locking means affixed to the storage device and configured to mate with a corresponding coupling on the infusion device when the data connector is connected with the corresponding data connector on the infusion device;

obtaining a central processing unit; and obtaining the infusion device further comprising:
- a fastener coupling configured to mate with a corresponding coupling on the programming key; and
- a storage device reader comprising a data connector configured to mate with a corresponding data connector on the storage device;

mating the storage device data connector with the infusion device data connector, communicating the digital key, the priming sequence and the medical treatment parameter to the infusion device, and communicating the medical treatment parameter from the infusion device to the data hub device.

17. A method according to claim 16 wherein:

the step of communicating the medical treatment parameter to the infusion device is followed by the step of sensing a medical treatment parameter during or following the medical treatment, and the step of communicating the medical treatment parameter from the infusion device to the data hub device further comprises the step of communicating the sensed medical treatment parameter to the data hub device.

\* \* \* \* \*